United States Patent [19]

Kluge

[11] 4,405,622
[45] Sep. 20, 1983

[54] [1-(1,4-BENZODIOXAN-2-YL)-4-(4-AMINOPYRIMIDIN-2-YL]PIPERAZINES USEFUL AS ANTI-DEPRESSANTS

[75] Inventor: Arthur F. Kluge, Los Altos, Calif.

[73] Assignee: Syntex (U.S.A.) Inc., Palo Alto, Calif.

[21] Appl. No.: 197,425

[22] Filed: Oct. 16, 1980

[51] Int. Cl.³ .................. A61K 31/495; C07D 405/14
[52] U.S. Cl. ...................................... 424/250; 544/295
[58] Field of Search ......................... 544/295; 424/250

[56] References Cited

U.S. PATENT DOCUMENTS

| 2,979,511 | 4/1961 | Krapcho | 260/309.6 |
| 3,360,529 | 12/1967 | Smith Kline | 260/340.3 |
| 3,829,441 | 8/1974 | Smith Kline | 260/340.3 |
| 3,944,549 | 3/1976 | Lafon | 260/256.4 |
| 3,959,283 | 5/1976 | Lafon | 260/268 |

FOREIGN PATENT DOCUMENTS

| 643853 | 8/1964 | Belgium . |
| 837386 | 5/1976 | Belgium . |
| 731147 | 3/1966 | Canada . |
| 54-103893 | 8/1979 | Japan . |
| 55-15455 | 2/1980 | Japan . |
| 55-15456 | 2/1980 | Japan . |
| 730718 | 12/1973 | Netherlands . |
| 641622 | 7/1964 | South Africa . |
| 1051143 | 12/1966 | United Kingdom . |
| 1094982 | 12/1967 | United Kingdom . |

Primary Examiner—Stanley J. Friedman
Attorney, Agent, or Firm—Hana Dolezalova; Tom M. Moran; Alan M. Krubiner

[57] ABSTRACT

Novel [1-(1,4-benzodioxan-2-yl)-4-(4-aminopyrimidin-2-yl]piperazines having the general formula

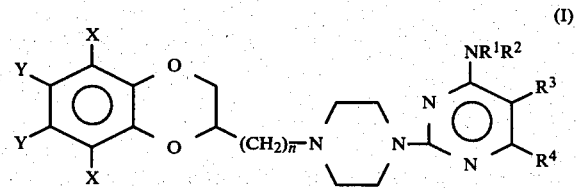

wherein:
$R^1$, $R^2$, $R^3$ and $R^4$ are independently selected from the group consisting of hydrogen and lower alkyl;
X and Y are independently selected from the group consisting of hydrogen, lower alkyl, lower alkoxy or halogen; and n is either 0, 1 or 2 and the pharmaceutically acceptable acid addition salts thereof are useful as anti-depressants.

9 Claims, No Drawings

[1-(1,4-BENZODIOXAN-2-YL)-4-(4-AMINOPYRIMI-DIN-2-YL]PIPERAZINES USEFUL AS ANTI-DEPRESSANTS

BACKGROUND OF THE INVENTION

1. Field of the Invention

The present invention is concerned with compounds in which a 1,4-benzodioxanyl moiety is linked to cyclic nitrogenous bases. More specifically, such compounds have the general formula

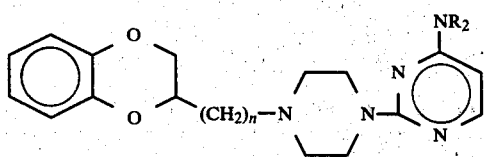

wherein the aromatic rings may be further substituted.

The invention concerns the compounds themselves, their preparation, compositions containing said compounds suitable for use as anti-depressants; and methods for preventing, inhibiting, or reducing depression.

2. Prior Art

A large number of compounds, in which the 1,4-benzodioxane system is substituted at the 2-position by a side chain containing nitrogen have been prepared, and shown to be active either in the central nervous system and/or the cardiovascular system. There appears to be no standard assay system for discriminating among the various types of effects of compounds on these target tissues; therefore the prior art is often non-specific as to the exact mode of action of the compounds tested. However, a variety of compounds having the general formula

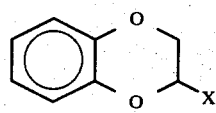

where X contains nitrogen in fairly close proximity to the ring are physiologically active. None is entirely satisfactory as an antidepressant. Those preparations closest in structure to the present invention are described in South African Pat. No. 64/622, Canadian Pat. No. 731,147, Belgian Pat. Nos. 643,853 and 837,386, U.S. Pat. Nos. 2,979,511, 3,360,529, 3,829,441, and 3,959,283 British Pat. Nos. 1,051,143 and 1,094,982, Japanese Pat. Nos. 54/103,893, 55/015,456 and 55/015,455, and Dutch Pat. No. 730,718.

Belgian Pat. No. 806380 (U.S. Pat. No. 3,944,549) discloses the compound

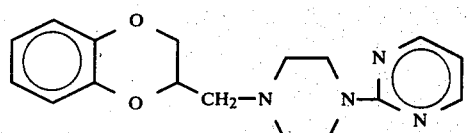

i.e. [1-(1,4-benzodioxan-2-ylmethyl)-4-(2-pyrimidinyl)]piperazine.

SUMMARY OF THE INVENTION

One aspect of the present invention relates to compounds of the general formula

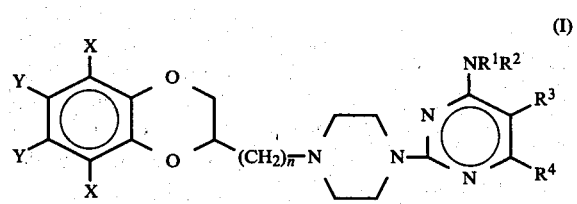

and the pharmaceutically acceptable acid addition salts thereof; wherein:

$R^1$, $R^2$, $R^3$ and $R^4$ are independently selected from the group consisting of hydrogen and lower alkyl;

X and Y are independently selected from the group consisting of hydrogen, lower alkyl, lower alkoxy or halogen; and n is either 0, 1 or 2.

A second aspect of the present invention relates to the methods of preparation of the above-mentioned compounds.

A third aspect concerns compositions suitable for pharmaceutical use as antidepressants which contain as active ingredient, a compound selected from the set herein described.

A fourth aspect concerns methods for using the compounds described herein as antidepressants.

DETAILED DESCRIPTION OF THE INVENTION

Definitions

As used herein, "lower alkyl" means a branched or unbranched saturated hydrocarbon chain containing 1-6 carbon atoms.

"Lower alkoxy" means -OR wherein R is lower alkyl as herein defined.

"Halogen" means fluorine, chlorine or bromine.

"Pharmaceutically acceptable salt" of the subject bases refers to those salts which retain the therapeutic properties of the free bases and which are neither biologically or otherwise undesired, formed with, for example, inorganic acids such as hydrochloric acid, hydrobromi acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid, and the like.

GENERAL ASPECTS OF PREPARATION

All of the benzodioxan-2-yl compounds described herein contain least one chiral center—i.e. the 2-position in the benzodioxane moiety at which the nitrogen containing ring system is attached. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein my be resolved into their optical antipodes by conventional resolution means known per se, for example, by the separation (e.g., fractional crystallization) of the diastereomeric salts formed by reaction of e.g., racemic compounds of Formula I with an optically active acid. Exemplary of such optically active acids are optically active forms of camphor-10-sulfonic acid, α-bromo-camphor-π-sulfonic acid, camphoric acid, menthoxy-acetic acid, tartaric acid malic acid, diacetyltartaric acid, pyrrolidone-5-carboxylic acid, and the like. The spearated pure diastereomeric salts may then be cleaved by standard means to afford the respective optical isomers of the free bases e.g. compounds of Formula I.

PREPARATION SCHEME

Members of the subject class of compounds may be prepared according to the following reaction scheme:

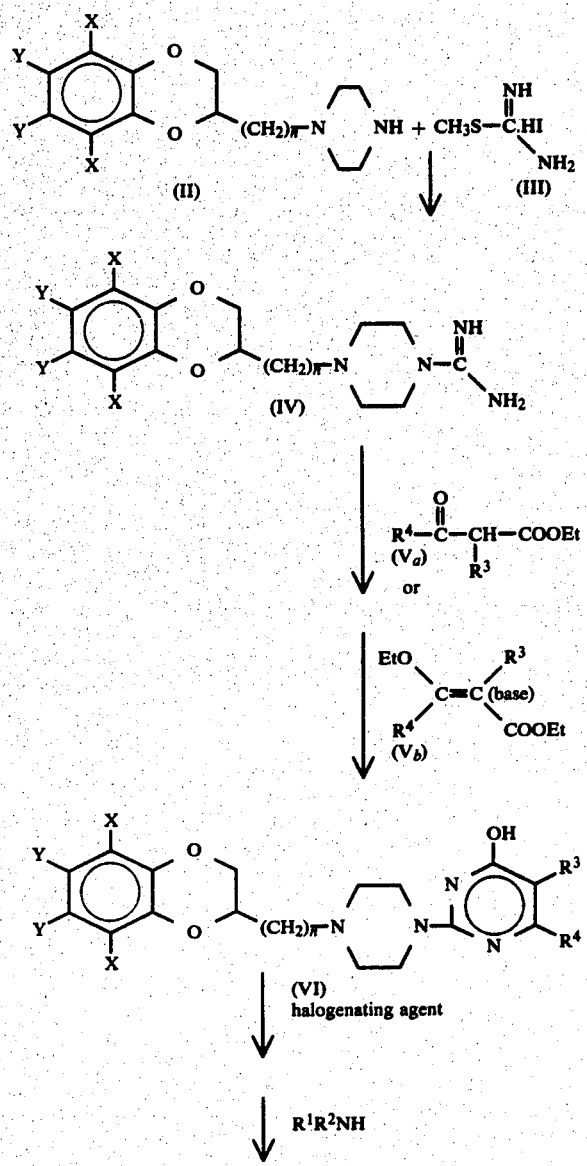

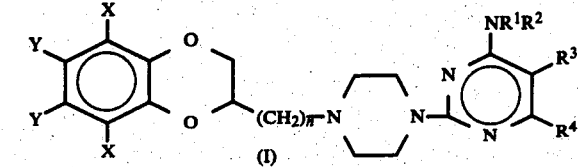

Compound V may either be the β-keto ester or the β-ethoxy acrylate, which is shown in the trans form for clarity, but cis may also be used.

The reaction scheme above shows the product in the form of the free base, but it is to be understood that the product and intermediates may, where appropriate, be isolated or recovered in the form of the acid addition salt.

Since many of the compounds in base form are oils or gums, it is often more convenient to isolate and characterize the compounds as acid addition salts. These salts are prepared in the usual manner, i.e., by reaction of the base compound with a suitable inorganic or organic acid, described above. Salts formed with dibasic acids (e.g. oxalic acid) may contain one or two molecules of base per molecule of acid. If desired, the salts may be readily converted to the compounds in base form by treatment with alkali, such as potassium carbonate, sodium carbonate or sodium or potassium hydroxide.

Isolation of the compounds described herein, whether in the body of the specification or Examples, can be effected, if desired, by an suitable separation or purification procedure, such as, for example, filtration, extraction, crystallization, column chromatography, thin-layer chromatography or thick-layer chromatography, or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures are evaporated to dryness, and the salts can be further purified by conventional methods.

Details of Preparation

Compounds of the Formula II, the starting material in the above Reaction Scheme are prepared according to the method described in British Pat. Nos. 1,520,801, 1,411,531 and 1,457,038 which follow the method of Toldy et al. *Acta Chimica Acadamiae Scienciarium Hungaricae* 49; 265 (1966).

Methyl isothiourea hydroiodide (III) is prepared by the reaction of thiourea with methyl iodide.

II, in its free base form is mixed with an approximately equimolar quantity of III in the presence of a polar solvent, such as ethanol, methanol, water and the like; preferably a mixture of methanol and water. The mixture is then heated to about 60°–100°, preferably 85°–95° for a number of hours, preferably overnight. The product (IV) is collected and isolated by conventional means—preferably as the acid addition salt.

The intermediate IV, preferably as an acid addition salt is then treated with an approximately equimolar amount of the β-ethoxyacrylate or β-keto ester (V) in the presence of a suitable base preferably a metal hydride in the presence of a suitable aprotic solvent, such as, e.g. DMSO, DMF or DME. The mixture is heated to reflux for several hours, preferably overnight, and the crude product (VI) may be isolated and purified if desired.

The hydropyrimidine VI is converted to the final product I, by a two step procedure in which the 4-hydroxyl on the pyrimidine ring is first converted to the halide by treatment with a suitable halogenating agent, such as, e.g. $PBr_3$; $PCl_5$, $POCl_3$; etc., preferably $POCl_3$. An excess of the halogenating agent is heated with VI for several hours, preferably 0.5-2.5 hours, and the intermediate halide may then be isolated if desired from the reaction mixture and purified by conventional methods. The halide is then treated with ammonia or a suitable 1° or 2° amine in the presence of a polar solvent, such as EtOH. The mixture is comprised of the halide with an excess of the ammonia or amine, and is heated for several hours, preferably to a temperature in the range of about 150°-170°, and preferably overnight.

The product, I, is isolated as the free base or as the salt.

Formulation and Administration

The compounds of Formula (I) and the pharmaceutically acceptable acid addition salts thereof exhibit CNS activity, and, in particular, are antidepressants. Said compounds have been shown to be $\alpha_2$ blockers in standard laboratory tests using pithed rats as subjects. Accordingly these compounds and pharmaceutically acceptable compositions containing them are useful in prevention, reduction and inhibition of depression in humans.

Administration of the active compounds and salts described herein can be via any of the accepted modes of administration for agents which relieve depression or affect the central nervous system including oral, parenteral and otherwise systemic in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula (I) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1-10 mg/kg/day, preferably 1-5 mg/kg/day. For an average 70 kg human, this would amount to 7-700 mg per day, or preferably 70-350 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compound of Formula (I) or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%-95% active ingredient, preferably 25-70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such compositions is highly dependent on the specific nature thereof, as well as the activity of the compound and the needs of the subject. However, percentages of active ingredient of 0.25% to 10% are employable, (higher if the composition is a solid which will be subsequently diluted to the above percentages), preferably in the range of 1-2%.

For systemic administration via suppository, traditional binders and carriers include, e.g. polyalkylene glycols or triglycerides. Such suppositories may be formed from mixtures containing active ingredient in the range of 0.5%-10%; preferably 1-2%.

PREFERRED EMBODIMENTS

A preferred class of compounds of the present invention is that wherein, in the general formula

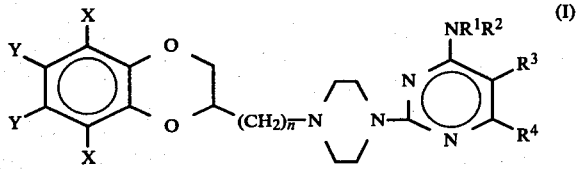

X and Y are hydrogen.

Another preferred class is that wherein $R^3$ and $R^4$ are hydrogen, and $R^3$ and $R^4$ are independently hydrogen or lower alkyl.

A more preferred class is that wherein X and Y, $R^1$ and $R^2$ are hydrogen, and $R^3$ and $R^4$ are independently hydrogen or lower alkyl.

A still more preferred class is that wherein X, Y, $R^1$, $R^2$, $R^3$ and $R^4$ are all hydrogen i.e. the compound embodying the invention is selected from the group consisting of:

[1-(1,4-benzodioxan-2-yl)-4-(4-aminopyrimidin-2-yl)]piperazine;
[1-(1,4-benzodioxan-2-ylmethyl)-4-(4-aminopyrimidin-2-yl]piperazine;
[1-[2-(1,4-benzodioxan-2-yl)ethyl]-4-(4-aminopyrimidin-2-yl)]piperazine.

In all of the above embodiments, the compound may be the free base or the pharmaceutically acceptable acid addition salt thereof.

PREPARATION I

Preparation of
[1-(1,4-benzodioxan-2-ylmethyl)-4-imidino]piperazine
and its salt A. 33.0 g of the salt: 1-(1,4-benzodioxan-2-ylmethyl)-piperazine.2 HCl was converted to the free base form by treating with aqueous NaOH. The free base was extracted into methylene chloride and the extract dried over $Na_2SO_4$. Evaporation of the solvent yielded 24.4 g of 1-(1,4-benzodioxan-2-yl)piperazine.

The entire yield was mixed with 50 ml water, and 22.7 g of methyl isothiourea.HI added. The mixture was heated to 75°, 50 ml methanol added, and the mixture allowed to reflux at 90° overnight. Solvent was then removed at reduced pressure and the precipitated product collected by filtration and washed with water. Residual water was removed by drying in an oven, giving 13.4 g of product, [1-(1,4-benzodioxan-2-ylmethyl)-4-imidino]-piperazine.HI., m.p. 240°–246° (d).

B. In similar manner, substituting into the procedure of part A in place of 1-(1,4-benzodioxan-2-ylmethyl)piperazine salts of the following compounds:
1-(6,7-dimethyl-1,4-benzodioxan-2-ylmethyl)piperazine;
1-(5,8-dichloro-6,7-di-n-butyl-1,4-benzodioxan-2-ylmethyl)piperazine;
1-(5,8-dimethyl-6,7-dibromo-1,4-benzodioxan-2-ylmethyl)piperazine;
1-(5,8-dimethoxy-1,4-benzodioxan-2-ylmethyl)piperazine; one obtains:
[1-(6,7-dimethyl-1,4-benzodioxan-2-ylmethyl)-4-imidino]piperazine;
[1-(5,8-dichloro-6,7-di-n-butyl-1,4-benzodioxan-2-ylmethyl)-4-imidino]piperazine;
[1-(5,8-dimethyl-6,7-dibromo-1,4-benzodioxan-2-ylmethyl)-4-imidino]piperazine;
[1-(5,8-dimethoxy-1,4-benzodioxan-2-ylmethyl)-4-imidino]piperazine.

C. Similarly, substituting into the procedure of Part A in place of 1-(1,4-benzodioxan-2-ylmethyl)piperazine, the compounds:
1-(1,4-benzodioxan-2-yl)piperazine and
1-[2-(1,4-benzodioxan-2-yl)ethyl]piperazine one obtains;
[1-(1,4-benzodioxan-2-yl)-4-imidino]piperazine and
[1-[2-(1,4-benzodioxan-2-yl)ethyl]-4-imidino]piperazine.

EXAMPLE 1

Preparation of
[1-(1,4-benzodioxan-2-ylmethyl)-4-(4-hydroxypyrimidine-2-yl)]piperazine A. 13.0 g of the thus prepared [1-(1,4-benzodioxan-2-ylmethyl)-4-imidino]piperazine.HI was mixed with 4.6 g of ethyl β-ethoxyacrylate and 3.12 g of 50% NaH in 75 ml dimethoxyethane, (DME). The mixture was refluxed overnight, solvent removed, and the residue mixed with 150 ml water. The water mixture was extracted with 2×50 ml hexane to remove impurities, acidified with HCl, and the pH finally adjusted with sodium bicarbonate. The crude product was extracted into 3×50 ml of $CH_2Cl_2$ and the solvent evaporated off. The residue was filtered through 50 g of silica containing 10% $CH_3OH$-$CH_2Cl_2$. The solvent was removed from the filtrate and the residue triturated with diethyl ether. Evaporation of the ether yielded 6.95 g of the intermediate [1-(1,4-benzodioxan-2-ylmethyl)-4-(4-hydroxy pyrimidin-2-yl)]piperazine, m.p. 169°–171°.

B. Similarly, substituting into the procedure of part A. the compounds listed in Preparation I parts B and C, one obtains:
[1-(6,7-dimethyl-1,4-benzodioxan-2-ylmethyl)-4-(4-hydroxypyrimidin-2-yl)]piperazine;
[1-(5,8-dichloro-6,7-di-n-butyl-1,4-benzodioxan-2-ylmethyl)-4-(4-hydroxypyrimidin-2-yl)]piperazine;
[1-(5,8-dimethyl-6,7-dibromo-1,4-benzodioxan-2-ylmethyl)-4-(4-hydroxypyrimidin-2-yl)]piperazine;
[1-(5,8-dimethoxy-1,4-benzodioxan-2-ylmethyl)-4-(4-hydroxypyrimidin-2-yl)]piperazine;
[1-(1,4-benzodioxan-2-yl)-4-(4-hydroxyprimidin-2-yl)]piperazine;
[1-[2-(1,4-benzodioxan-2-yl)ethyl]-4-(4-hydroxypyrimidin-2-yl)]piperazine.

C. Similarly, substituting into the procedure of part A, for ethyl β-ethoxyacrylate, the compounds:
ethyl 2-n-butyl-3-ethoxyhept-2-enoate;
ethyl 2-n-butyl-3-ethoxybut-2-enoate;
ethyl 2-methyl-3-ethoxyacrylate;
ethyl 3-ethoxyhept-2-enoate;
one obtains:
[1-(1,4-benzodioxan-2-ylmethyl-4-(5,6-di-n-butyl-4-hydroxypyrimidin-2-yl)]piperazine;
[1-(1,4-benzodioxan-2-ylmethyl-4-(6-methyl-5-n-butyl-6-hydroxypyrimidin-2-yl)]piperazine;
[1-(1,4-benzodioxan-2-ylmethyl-4-(5-methyl-4-hydroxypyrimidin-2-yl)]piperazine;
[1-(1,4-benzodioxan-2-ylmethyl-4-(6-n-butyl-4-hydroxypyrimidin-2-yl)]piperazine.

EXAMPLE 2

Preparation of
[1-(1,4-benzodioxan-2-ylmethyl)-4-(4-aminopyrimidin-2-yl)]piperazine A. To a 6.5 g sample of the intermediate prodouct of Example 1 part A was added 50 ml $POCl_3$. The mixture was heated at 110° for 1½ hours, and the excess POCl₃ then removed by vacuum distillation. The residue was suspended in ice-NH₄OH, and the product extracted into CH₂Cl₂. The solvent CH₂Cl₂ was removed by evaporation, and the residue filtered through 25 g SiO₂ with diethyl ether. The filtrate was then subjected to evaporation to remove solvent; the residue was 6.75 g of an oil, which solidified on standing.

A 3 g sample of the oil was taken up in methanolether and converted to the hydrochloride by bubbling in excess HCl. A white solid precipitates; [1-(1,4-benzodioxan-2-ylmethyl)-4-(4-chloropyrimidin-2-yl)]piperazine.HCl, m.p. 93.94°.

2.65 g of the above chloropyrimidine salt was treated with 25 ml of 25% NH₃ in ethanol, and heated at 170° overnight in a high pressure vessel. The mixture was cooled and the solvent removed under reduced pressure. To the residue was added 50 ml 1% NaOH, and the product was extracted with methylene chloride. The CH₂Cl₂ solvent was then removed and the residue filtered therethrough 10 g silica gel containing 10% methanol-methylene chloride. Solvent was removed from the filtrate and the residue triturated with ether. Upon evaporation of the ether extract, 1.7 g of crystalline [1-(1,4-benzodioxan-2-ylmethyl)-4-(4-amino-pyrimidin-2-yl]piperazine, m.p. 149°–150° was obtained.

The crystals were converted to the hydrochloride salt by dissolving in CH₃OH-ethyl acetate, bubbling through an excess of dry HCl, and filtering out the precipitated hydrochloride. The resulting dihydrochloride melted at 240°–243°.

B. Similarly, substituting into the procedure of part A in place of [1-(1,4-benzodioxan-2-ylmethyl)-4-(4-hydroxypyrimidin-2-yl]piperazine the compounds listed in part B, Example 1, one obtains:
[-(6,7-dimethyl-1,4-benzodioxan-2-ylmethyl)-4-(4-aminopyrimidin-2-yl)]piperazine;
[1-(5,8-dichloro-6,7-di-n-butyl-1,4-benzodioxan-2-ylmethyl)-4-(4-aminopyrimidin-2-yl)]piperazine;
[1-(5,8-dimethyl-6,7-dibromo-1,4-benzodioxan-2-ylmethyl)-4-(4-aminopyrimidin-2-yl)]piperazine;
[1-(5,8-dimethoxy-1,4-benzodioxan-2-ylmethyl)-4-(4-aminopyrimidin-2-yl)]piperazine;
[1-(1,4-benzodioxan-2-yl)-4-(4-aminopyrimidin-2-yl)]piperazine;
[1-[2-(1,4-benzodioxan-2-yl)ethyl]-4-(4-aminopyrimidin-2-yl)]piperazine.

C. Similarly, substituting into the procedure of part A, in place of [1-(1,4-benzodioxan-2-ylmethyl)-4-(4-hydroxypyrimidin-2-yl]piperazine the compounds listed as prepared in Example 1, part C, one obtains:
[1-(1,4-benzodioxan-2-ylmethyl)-4-(5,6-di-n-butyl-4-aminopyrimidin-2-yl)]piperazine;
[1-(1,4-benzodioxan-2-ylmethyl)-4-(6-methyl-5-n-butyl-4-aminopyrimidin-2-yl)]piperazine;
[1-(1,4-benzodioxan-2-ylmethyl)-4-(5-methyl-4-aminopyrimidin-2-yl)]piperazine;
[1-(1,4-benzodioxan-2-ylmethyl)-4-(6-n-butyl-4-aminopyrimidin-2-yl)]piperazine.

D. Similarly, substituting into the procedure of part A in place of ammonia, dimethylamine di-n-butylamine or methyl, ethylamine, one obtains:
[1-(1,4-benzodioxan-2-yl)-4-(4-N,N-dimethylaminopyrimidin-2-yl)]piperazine;
[1-(1,4-benzodioxan-2-yl)-4-(4-N,N-di-n-butylaminopyrimidin-2-yl)]piperazine;
[1-(1,4-benzodioxan-2-yl)-4-(4-N-methyl-N-ethylaminopyrimidin-2-yl)]piperazine.

EXAMPLE 3

Preparation of [1-(1,4-benzodioxan-2-ylmethyl)-4-(6-methyl-4-hydroxypyrimidine-2-yl)]piperazine To 250 ml ethanol is added 4.6 g sodium metal. After the sodium has dissolved, 13.0 g of ethyl acetoacetate is added over 15 minutes. 30.0 g of the [1-(1,4-benzodioxan-2-ylmethyl)-4-imidine]piperazine.HI from preparation I is added, and the resulting mixture is heated at reflux for 16 hours.

The solvent is removed, and the residue mixed with 200 ml water, and neutralized by first acidifying with HCl and neutralizing with NaHCO₃. The crude product was extracted into 3×50 ml of CH₂Cl₂ and the solvent evaporated off. The residue was filtered through 50 of silica containing 10% CH₃OH-CH₂Cl₂. The solvent was removed from the filtrate and the residue triturated with diethyl ether. Evaporation of the ether yields the product, [1-(1,4-benzodioxan-2-ylmethyl)-4-(6-methyl-4-hydroxypyrimidine-2-yl)]piperazine.

EXAMPLE 4

Conversion of Free Base to Salt

Ethereal hydrogen chloride is added dropwise to a solution of 1.0 g [1-(1,4-benzodioxan-2-ylmethyl)-4-(4-aminopyrimidin-2-yl)]piperazine in 100 ml CH₃OH-ethyl acetate until precipitation is complete. The product is filtered, washed with ether, air dried and recrystallized from methanol/acetone to yield 1,4-benzodioxan-2-yl hydrochloride, m.p. 240°–243°.

In a similar manner, all compounds of formula (I) and intermediates in preparation thereof in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 5

Conversion of an Addition Salt to the Free Base

[1-(1,4-benzodioxan-2-ylmethyl)-4-(4-aminopyrimidin-2-yl)]piperazine hydrochloride (1.0 g) suspended in 50 ml of ether is stirred with excess dilute aqueous potassium carbonate solution until the salt is completely dissolved. The organic layer is then separated, washed twice with water, dried over magnesium sulfate and evaporated to yield [1-(1,4-benzodioxan-2-ylmethyl-4-(4-aminopyrimidin-2-yl)]piperazine, m.p. 149°–150°.

In a similar manner the acid addition salts of all compounds of formula (I) and of intermediates in the preparation thereof may be converted to the corresponding compounds in free base form.

EXAMPLE 6

Direct interchange of acid addition salts of [1,4-benzodioxan-2-ylmethyl)-4-(4-aminopyrimidin-2-yl)]piperazine

[1-(1,4-benzodioxan-2-ylmethyl)-4-(4-aminopyrimidin-2-yl)]piperazine hydrochloride (1.0 g) is dissolved in 50 ml 50% aqueous sulfuric acid, and the solution evaporated to dryness. The product is suspended in ethanol and filtered, air dried and recrystallized from methanol-/acetone to yield [1-(1,4-benzodioxan-2-yl-methyl)-4-(4-aminopyrimidin-2-yl)]-piperazine hydrosulfate.

In Examples 7 through 10, the active ingredient is [1-(1,4-benzodioxan-2-ylmethyl)-4-(4-aminopyrimidin-2-yl)]piperazine imidazole hydrochloride. Other compounds of Formula (I) and the pharmaceutically acceptable salts thereof may be substituted therein.

EXAMPLE 7

| Composition for Oral Administration | |
|---|---|
| The composition contains: | % wt./wt. |
| Active ingredient | 95% |
| Lactose | 5% |

The two ingredients are milled, mixed and dispensed into capsules containing 100 mg each; one capsule would approximate a total daily dosage.

EXAMPLE 8

| Composition for Oral Administration | |
|---|---|
| The composition contains: | % wt./wt. |
| Active ingredient | 56.8% |
| Magnesium stearate | 0.9% |
| Starch | 8.6% |
| Lactose | 32.9% |
| PVP (polyvinylpyrrolidine) | 0.9% |

The above ingredients are combined and granulated using methanol as solvent. The formulation is then dried and formed into tablets (containing 200 mg of active compound) with an appropriate tableting machine.

EXAMPLE 9

| Parenteral Formulation (IV) | |
|---|---|
| The composition contains: | % wt./wt. |
| Active compound | 0.25 g |
| Propylene glycol | 20. g |
| Polyethylene glycol 400 | 20. g |
| Polysorbate 80 | 1. g |
| 0.9% Saline solution qs ad | 100 ml |

The active compound is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 10

| Suppository Formulation | |
|---|---|
| The composition contains: | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

We claim:

1. A composition for reducing, inhibiting or preventing depression in humans which comprises an effective amount of a compound of the formula

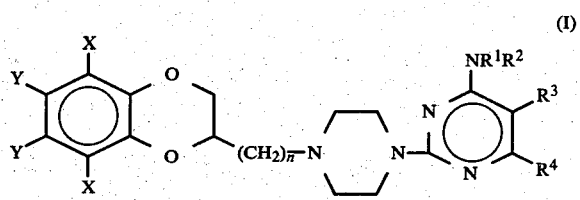

or the pharmaceutically acceptable acid addition salts thereof wherein:
 $R^1$, $R^2$, $R^3$ and $R^4$ are independently selected from the group consisting of hydrogen and lower alkyl;
 X and Y are independently selected from the group consisting of hydrogen, lower alkyl, lower alkoxy or halogen; and n is either 0, 1 or 2, in admixture with at least one pharmaceutically acceptable excipient.

2. A method for preventing, inhibiting or reducing depression in humans, which comprises administering to a subject in need of such treatment an effective amount of, or a pharmaceutical composition containing an effective amount of, a compound of the formula

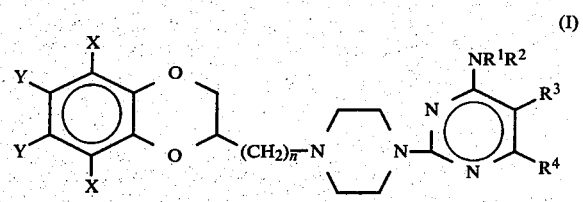

wherein
 $R^1$, $R^2$, $R^3$ and $R^4$ are independently selected from the group consisting of hydrogen and lower alkyl;
 X and Y are independently selected from the group consisting of hydrogen, lower alkyl, lower alkoxy or halogen; and n is either 0, 1 or 2.

3. A compound having the formula

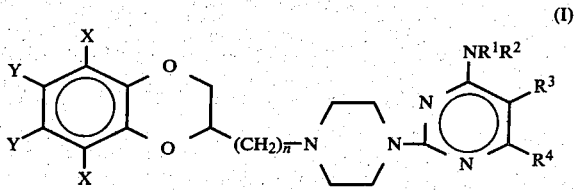

and the pharmaceutically acceptable acid addition salts thereof wherein:
 $R^1$, $R^2$, $R^3$ and $R^4$ are independently selected from the group consisting of hydrogen and lower alkyl;
 X and Y are independently selected from the group consisting of hydrogen, lower alkyl, lower alkoxy or halogen; and n is either 0, 1 or 2.

4. The compound of claim 1 and the pharmaceutically acceptable acid addition salts thereof wherein X and Y are hydrogen.

5. The compound of claim 1 and the pharmaceutically acceptable acid addition salts thereof wherein $R^1$ and $R^2$ are hydrogen; and $R^3$ and $R^4$ are independently hydrogen or lower alkyl.

6. The compound of claim 3 and the pharmaceutically acceptable acid addition salts thereof wherein X and Y are hydrogen.

7. The compound of claim 4, wherein $R^3$ and $R^4$ are hydrogen and n=0, [1-(1,4-benzodioxan-2-yl)-4-(4-aminopyrimidin-2yl)]-piperazine, and the pharmaceutically acceptable acid addition salts thereof.

8. The compound of claim 4 wherein $R^3$ and $R^4$ are hydrogen, and n=1; [1-(1,4-benzodioxan-2-yl-methyl)-4-(4-aminopyrimidin-2-yl)]piperazine and the pharmaceutically acceptable acid addition salts thereof.

9. The compound of claim 4, wherein $R^3$ and $R^4$ are hydrogen and n=2, [1-[2-(1,4-benzodioxan-2-yl)-ethyl]-4-(4-aminopyrimidin-2-yl)]-piperazine, and the pharmaceutically acceptable acid addition salts thereof.

* * * * *